《12》 United States Patent
Rüdinger et al.

(10) Patent No.: US 6,793,777 B1
(45) Date of Patent: Sep. 21, 2004

(54) METHOD FOR SEPARATING AND PURIFYING AN AQUEOUS MIXTURE THAT MAINLY CONSISTS OF ACETIC ACID AND FORMIC ACID

(75) Inventors: Christoph Rüdinger, Starnberg (DE); Harald Herbert Voit, Reischach (DE); Michael Hallmann, Hochburg-Ach (AT); Mehmet Günaltay, Emmerting (DE); Barbara Reil, Emmerting (DE); Hans-Jürgen Eberle, München (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 298 days.

(21) Appl. No.: 10/009,507

(22) PCT Filed: Jun. 29, 2000

(86) PCT No.: PCT/EP00/06092

§ 371 (c)(1),
(2), (4) Date: Dec. 5, 2001

(87) PCT Pub. No.: WO01/07391

PCT Pub. Date: Feb. 1, 2001

(30) Foreign Application Priority Data

Jul. 22, 1999 (DE) .......................................... 199 34 410

(51) Int. Cl.[7] .......................... B01D 3/14; B01D 11/00; C07C 51/46; C07C 51/44; C07C 53/02

(52) U.S. Cl. ............................ 203/14; 203/15; 203/16; 203/25; 203/27; 203/73; 203/78; 203/80; 203/84; 203/99; 203/DIG. 8; 203/DIG. 19; 562/608; 562/609

(58) Field of Search ................................ 203/43–46, 14, 203/15–16, 73–75, 77–78, 80, 84, 99, DIG. 19, DIG. 8, 25, 27; 562/608, 609, 513

(56) References Cited

U.S. PATENT DOCUMENTS 3,718,545 A * 2/1973 Horlenko ...................... 203/15
4,081,355 A * 3/1978 Preusser et al. ............ 208/313

(List continued on next page.)

FOREIGN PATENT DOCUMENTS

CA 1 238 919 7/1988
DE 1204 214 6/1966

(List continued on next page.)

OTHER PUBLICATIONS

English Derwent Abstract AN 1996–078095 corresponding to DE 44 26 132.

(List continued on next page.)

Primary Examiner—Virginia Manoharan
(74) Attorney, Agent, or Firm—Collard & Roe, P.C.

(57) ABSTRACT

The invention relates to a method for separating and purifying an aqueous mixture that mainly consists of acetic acid, formic acid and high-boiling substances by extraction with a solvent in a cyclic process. The inventive method is characterized in that the flow of raffinate is fed to a solvent stripping column (11) with the major part of the water in order to remove the water from the cycle. The flow of extract is fed to a solvent recovery distillation column (8). In a first step, a mixture (A) that consists of water and solvent, is separated by overhead distillation. A mixture (B) that consists of acetic acid, formic acid and high-boiling substances is separated via a sump. Once the formic acid is removed in a column (29), mixture (B) is separated in an acetic acid distillation column to give pure acetic acid and high-boiling substances. Mixture (A) is fed to a phase separator and the aqueous phase is returned to the solvent stripping column (11) together with any residual portions of the solvent while the organic phase is returned to the extractor (8).

17 Claims, 3 Drawing Sheets

U.S. PATENT DOCUMENTS

| | | | | |
|---|---|---|---|---|
| 4,088,676 A | * | 5/1978 | Hofen et al. | 562/6 |
| 4,262,140 A | | 4/1981 | Bott et al. | |
| 4,661,208 A | * | 4/1987 | Honma et al. | 203/15 |
| 4,735,690 A | * | 4/1988 | Berg et al. | 203/51 |
| 4,877,490 A | | 10/1989 | Berg et al. | |
| 4,935,100 A | | 6/1990 | Berg et al. | |
| 5,006,205 A | | 4/1991 | Berg et al. | |
| 5,173,156 A | | 12/1992 | Berg et al. | |
| 5,633,402 A | | 5/1997 | Berg | |
| 5,662,780 A | | 9/1997 | Sasaki et al. | |

FOREIGN PATENT DOCUMENTS

| | | |
|---|---|---|
| DE | 44 26 132 | 1/1996 |
| DE | 196 10 356 | 4/1997 |
| EP | 0 012 321 | 8/1981 |
| EP | 0 156 309 | 6/1989 |
| EP | 0 732 320 | 9/1996 |
| EP | 0 635 474 | 4/1999 |
| GB | 735867 | 8/1955 |
| GB | 771992 | 4/1957 |
| GB | 788931 | 1/1958 |

OTHER PUBLICATIONS

Stanford Research Institute, Process Economics Program, 1973, Report No. 37A.

W. Hunsmann, K.H. Simmrock, Chemie–Ing.–Tech, 1966, 38, 1053–1059.

* cited by examiner

METHOD FOR SEPARATING AND PURIFYING AN AQUEOUS MIXTURE THAT MAINLY CONSISTS OF ACETIC ACID AND FORMIC ACID

CROSS REFERENCE TO RELATED APPLICATIONS

Applicant claims priority under 35 U.S.C. §119 of German Application No. 19934410.8 filed Jul. 22, 1999. Applicant also claims priority under 35 U.S.C. 365 of PCT/EP00/06092 filed Jun. 29, 2000. The international application under PCT article 21 (2) was not published in English.

BACKGROUND OF THE INVENTION

1. Field of the Invention

The invention relates to a process for the separation and purification of an aqueous reaction mixture comprising the main components acetic acid and formic acid.

2. The Prior Art

The preparation of acetic acid by catalytic oxidation of saturated and/or unsaturated hydrocarbons, for example the gas-phase oxidation of $C_4$-hydrocarbons, results in formation of product streams comprising as main components acetic acid, formic acid and water in varying proportions.

To work them up further, these product streams have to be separated into their individual components. Separation of a ternary acid/water mixture comprising acetic acid, formic acid and water into its pure components by distillation, for example, presents considerable problems since the system contains not only the binary water/formic acid maximum azeotrope but also a ternary water/formic acid/acetic acid saddle azeotrope.

If such a mixture has a high water concentration, separation by distillation has a tremendous additional energy requirement since all the water has to be distilled off at the top of a column as lowest-boiling component.

For the separation of aqueous mixtures having an acetic acid content of >60% by weight and a formic acid content of 5% by weight, Hunsmann and Simmrock (Chemie-Ing.-Tech., 38, 1966) recommend the use of azeotropic distillation for making the separation easier and for reducing the energy required. As azeotropic entrainer for the removal of water, ethyl n-butyl ether is proposed. The azeotrope of water and entrainer boils at about 91° C. and contains about 10% by weight of water. The entrainer ethyl n-butyl ether forms no azeotrope with formic acid and acetic acid.

For separating off formic acid, DE-A 1204214 recommends azeotropic rectification using n-butyl chloride as entrainer. The disadvantage of this process is the use of chlorinated hydrocarbons as entrainer.

U.S. Pat. No. 5,633,402 discloses a process for the separation of binary mixtures of formic acid and acetic acid by means of azeotropic distillation. Methyl formate is used as entrainer for the formic acid. Removal of water is not described in this process.

DE-A 4426132, EP-A 0635474, DE-A 19610356 (U.S. Pat. No. 5,662,780) disclose various processes for the purification and dewatering of acetic acid by means of azeotropes with various entrainers. However, none of these processes describes the dewatering of a mixture of acetic acid and formic acid.

U.S. Pat. No. 5,173,156, U.S. Pat. No. 5,006,205, U.S. Pat. No. 4,877,490 and U.S. Pat. No. 4,935,100 disclose processes for the dewatering of formic acid by means of extractive rectification. Entrainers mentioned here are, for example, cyclohexanone, oxalic acid, decanoic acid and methyl salicylate.

EP-A 156309 (CA-A 1238919) and EP-A 12321 (U.S. Pat. No. 4,262,140) describe the dewatering of formic acid by extractive rectification using carboxamides as auxiliaries. However, none of these processes describes the dewatering of a mixture of acetic acid and formic acid.

The "Process Economics Program" Report No. 37A (1973) of the Stanford Research Institute discloses a process for the separation of an aqueous mixture comprising about 42% by weight of acetic acid and 2% by weight of formic acid. In this process, the aqueous mixture is concentrated by countercurrent extraction with diisopropyl ether. In the dewatering and solvent recovery column, the water is distilled off at the top as an azeotrope of water and diisopropyl ether. The bottom product, namely a mixture of acetic acid and formic acid containing about 0.12% by weight of water, is fractionated further by azeotropic rectification. Benzene is used as entrainer for the formic acid. A great disadvantage of this process is the low quality of the formic acid separated off, which still contains about 1% by weight of acetic acid, about 2% by weight of water and about 7% by weight of benzene. The use of benzene in this process and the residual benzene content in the formic acid make this process unattractive.

All the processes known from the prior art are either only suitable for satisfactorily separating binary mixtures such as acetic acid/water, formic acid/water and acetic acid/formic acid or only economically applicable to aqueous acid mixtures in which a high concentration of acid (>60% by weight) is present. Furthermore, some of the known processes are no longer acceptable from the point of view of today's safety and environmental standards because of their use of benzene or chlorinated hydrocarbons.

SUMMARY OF THE INVENTION

It is therefore an object of the invention to provide a process for the separation of a ternary, aqueous mixture of acids into its pure components, which process does not have the disadvantages mentioned in the discussion of the prior art.

It has how been found that the separation and purification of a mixture comprising the main components acetic acid, formic acid, water and high boilers (hereinafter referred to as crude acid) can be carried out particularly readily if the mixture is extracted by means of a solvent in a circulation process in a first step and the extract stream consisting predominantly of solvent, acetic acid, formic acid, high boilers and water is subsequently fractionated in a sequence of distillation steps into the constituents solvent which is recirculated to the extraction, water, formic acid, acetic acid and high boilers, and the raffinate stream is freed of solvent in a further distillation step by means of a solvent stripping column.

The invention provides a process for the separation and purification of an aqueous mixture comprising the main components acetic acid, formic acid and high boilers by extraction with a solvent in a circulation process, which comprises feeding the raffinate stream containing a major part of the water to a solvent stripping column (11) for removal of the water and conveying the extract stream to a solvent distillation column (8) from which, in a first step, a mixture (A) comprising water and solvent is separated off via the top and a mixture (B) comprising acetic acid, formic acid and high boilers is separated off via the bottom, separating the formic acid off from the mixture (B) in column (29) and subsequently fractionating the remaining mixture (B) into pure acetic acid and high boilers in an acetic acid distillation column (5), and conveying the mixture (A) to a phase separator (25) from which the resulting aqueous phase containing residual solvent is recirculated to the solvent stripping column (11) and the organic phase is recirculated to the extractor (7).

Figure 1:
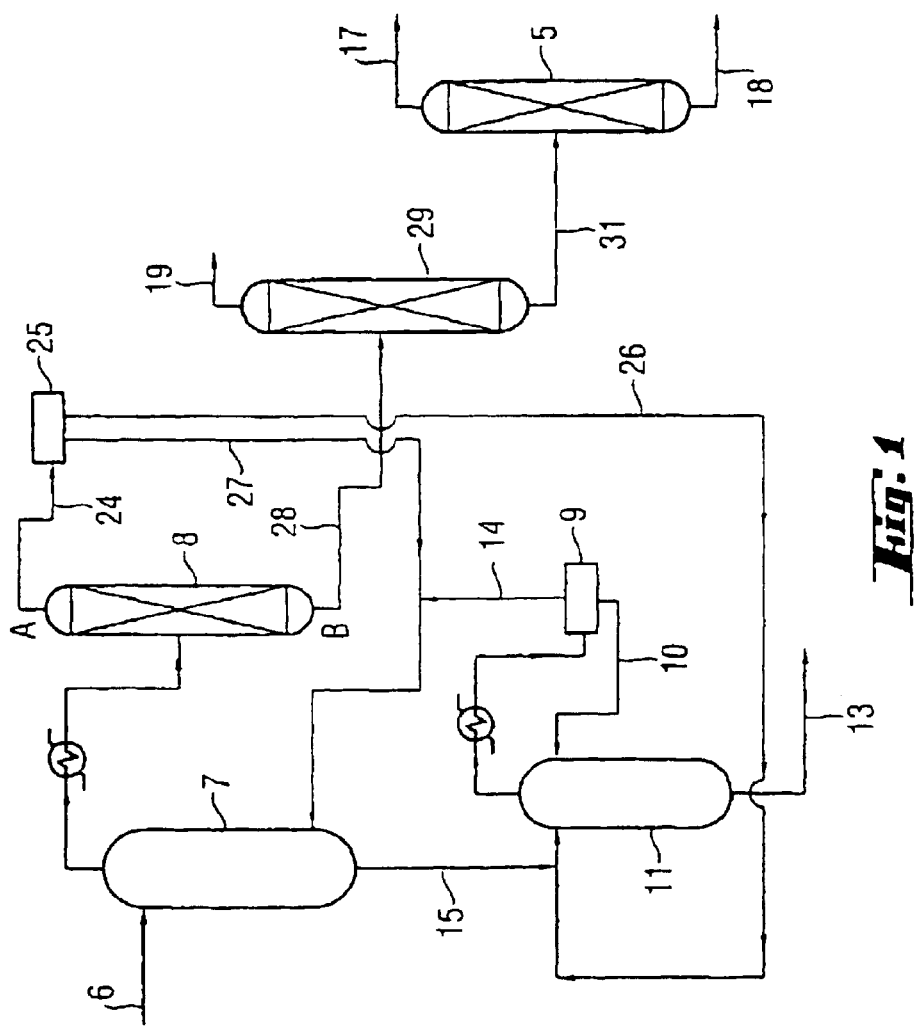
FIG. 1 shows an apparatus for carrying out the separation and purification process of the invention.

In the first step (extraction) of the process of the invention (FIG. 1), the crude acid feed comprising varying proportions of acetic acid, formic acid, water and high boilers is fed via a line (6) to an extractor (7) and brought into contact with a solvent. The extractor (7) can have a single-stage or preferably multistage configuration. The solvent stream can, in this process, be directed in the direction of flow of the crude acid or preferably be conveyed in countercurrent to the crude acid. Solvents which can be used here are ethers, esters, ketones, alcohols, saturated, unsaturated and cyclic hydrocarbons having from 4 to 8 carbon atoms and their mixtures, preferably ethers and esters having from 4 to 7 carbon atoms, particularly preferably methyl tert-butyl ether, diisopropyl ether, di-n-propyl ether, ethyl butyl ether, ethyl acetate and isopropyl acetate, in a mixing ratio to crude acid (volume/volume) of from 0.5 to 20, preferably from 1 to 5, particularly preferably from 1.5 to 3.5 (ratio volume/volume). The extraction can take place in a temperature and pressure range in which the extraction solvent and the crude acid are present in liquid form and as separate phases, i.e. with a miscibility gap. Preference is given to a temperature range from 0° C. to 60° C. and a pressure range from $1*10^5$ to $20*10^5$ Pa.

The raffinate obtained from the extractor (7) is fed via line (15) to the solvent stripping column (11) where pure water is taken off at the bottom (line (13)). The product from the top of the solvent stripping column is fed to a phase separator (9). The aqueous phase obtained there goes via line (10) back to the top of the solvent stripping column (11), while the organic phase obtained is recirculated via line (14) to the extractor (7).

The extract taken off from the extractor (7), comprising varying proportions of solvent, acetic acid, formic acid, water and high boilers, is conveyed from the extractor to a solvent distillation column (8).

The solvent distillation column (8) can be operated under atmospheric pressure, but preferably under superatmospheric pressure.

The solvent distillation column (a) is preferably operated under a pressure of $1*10^5$ to $50*10^5$ Pa, preferably from $1*10^5$ to $25*10^5$ Pa, particularly preferably from $1*10^5$ to $5*10^5$ Pa.

In this column, the extract is divided into two substreams by distillation. One substream (mixture (A)), comprising a mixture of solvent and water, is taken off at the top of the column and fed to a phase separator (25) (line (24)). The aqueous phase containing residual solvent is separated off via line (26), and fed to the solvent stripping column (11), preferably at the feed point of the raffinate. The organic phase is taken off via line (27) and recirculated to the extractor (7).

The second substream (mixture (B)) obtained from column (8), comprising the components acetic acid, formic acid and high boilers, is taken off at the bottom of the solvent distillation column (8) and introduced into an intermediate distillation column (29) (line 28)). The column (29) is likewise operated under atmospheric pressure, but preferably under superatmospheric pressure of from $1*10^5$ to $50*10^5$ Pa, more preferably from $1*10^5$ to $25*10^5$ Pa, particularly preferably from $1*10^5$ to $5*10^5$ Pa. From this column (29), the pure formic acid is taken off at the top via line (19). A mixture of acetic acid and high boilers which is free of formic acid is taken off at the bottom and conveyed via line (31) to an acetic acid distillation column (5) in which the remaining stream is fractionated into pure acetic acid and high boilers. The acetic acid is taken off at the top via line (17) and the high boilers are separated off at the bottom of the column via line (18).

In a particular embodiment (FIG. 2) of the process of the invention, the solvent distillation column (8) is operated in such a way that part of the water is also carried out at the bottom via line (28) and is conveyed together with the acetic acid, the formic acid and the high boilers to the intermediate distillation column (29). In this case, the water containing small amounts of acetic acid and formic acid is taken off from the distillation column (29) via an additional side offtake and line (35) and is discarded or recirculated via line (35) to the crude acid inlet (6) or another point on the extractor (7).

In this embodiment, the separation function in the solvent column (8) is significantly simplified compared to the process shown in FIG. 1 by the codischarge of water. Furthermore, the additional side offtake on the formic acid distillation column (29) also simplifies the separation into pure formic acid and the bottom product comprising acetic acid and high boilers.

In a further embodiment (FIG. 3) of the process of the invention, the solvent distillation column (8) is likewise operated in such a way that the substream (mixture (B)) separated off at the bottom via line (28) still contains small amounts of water in order to make the separation easier.

This bottom product, comprising acetic acid, formic acid and small amounts of water, is fractionated in an intermediate distillation column (29) into a bottom product which comprises acetic acid and high boilers and is free of formic acid and a mixed top product comprising formic acid, water and small amounts of acetic acid.

The product from the top of the distillation column (29), comprising formic acid, water and small amounts of acetic acid, is subsequently conveyed via line (19) to the pure formic acid distillation column (33). This column (33) is operated at a lower pressure than the intermediate distillation column (29). The pressure difference between column (33) and column (29) is from $0.1*10^5$ Pa to $25*10^5$ Pa, preferably from $0.5*10^5$ Pa to $5*10^5$ Pa. In the pure formic acid distillation column (33), the product stream is fractionated into pure formic acid via line (34) as top product and a mixed bottom product comprising acetic acid, formic acid and water. This bottom product is recirculated via line (32) to the extract stream or another feed point on the solvent distillation column (8).

The raffinate stream (15) from the extractor (7) and the aqueous phase (26) from the phase separation vessel (25) are conveyed to the solvent stripping column (11). Pure water is taken off at the bottom of this column via line (13). The product from the top of this column is conveyed to the phase separator (9). The organic phase obtained is recirculated to the extractor (7), and the aqueous phase is fed into the top of the stripper column (11) via line (10).

In this process variant, it is of great advantage that the demands made of the separation efficiency of the separation column (29) are significantly reduced by the additional pure formic acid distillation (33) under lower pressure than in the separation column (29). This results in a significant energy saving together with greatly improved formic acid purity compared with comparable processes. Furthermore, the heat of condensation of the distillation column (29) can be used in an integrated heat system for heating the formic acid distillation column (33) and the solvent column (11). The heat of reaction of the reactions preceding this separation process, for example a catalytic gas-phase oxidation of hydrocarbons, can likewise be used for heating the solvent distillation column (8), the distillation column (29), the formic acid distillation column (33) and the acetic acid distillation column (5).

DETAILED DESCRIPTION OF PREFERRED EMBODIMENTS

The following examples illustrate the process of the invention with reference to the figures:

Example 1

Figure 3:
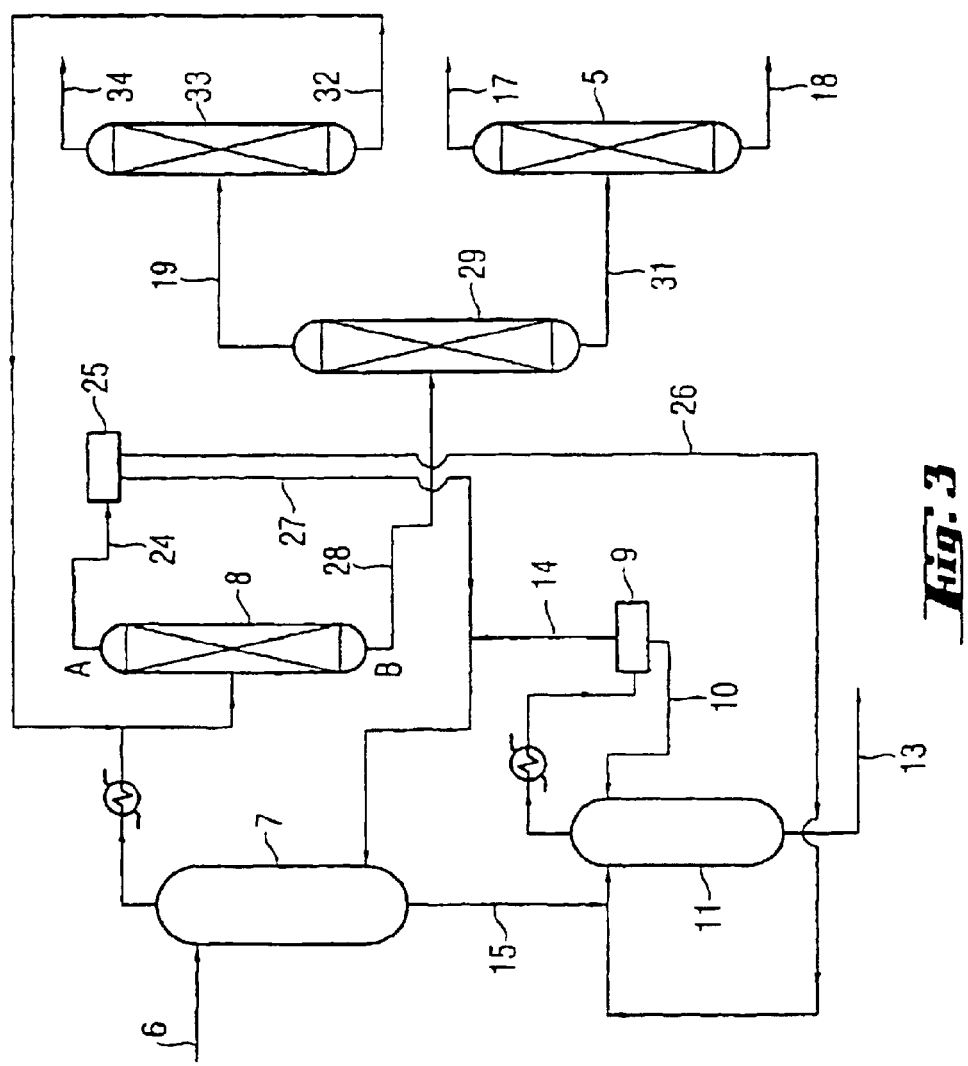
FIG. 3 shows the apparatus of FIG. 1 plus a formic acid distillation column.

In an apparatus corresponding to the embodiment of FIG. 3, a crude acid stream comprising 12.9 kg/h of acetic acid, 2.6 kg/h of formic acid, 48.4 kg/h of water and 0.8 kg/h of high boilers was fed via line (6) to the extractor (7) (countercurrent extraction column with stationary stainless steel packing, organic phase dispersed). Via line (27) and line (14), a solvent return stream containing 135.4 kg/h of methyl tert-butyl ether (MTBE), 4.0 kg/h of water, 0.5 kg/h of acetic acid and 0.2 kg/h of formic acid was fed to the extractor (7) in the steady state. The extract stream leaving the extractor (7) was composed of 133.9 kg/h of MTBE, 13.1 kg/h of acetic acid, 8.1 kg/h of water, 2.6 kg/h of formic acid and 0.1 kg/h of high boilers. The raffinate stream leaving the extractor (7) via line (15) was composed of 44.7 kg/h of water, 1.5 kg/h of MTBE, 0.4 kg/h of acetic acid, 0.2 kg/h of formic acid and 0.7 kg/h of high boilers.

The solvent distillation column (8) and the distillation column (29) were operated at a pressure of $2.75*10^5$ Pa. The pure formic acid column (33) and the pure acetic acid column (5) were operated at a pressure of $1*10^5$ Pa.

At the bottom of the solvent column (8), a stream comprising 13.4 kg/h of acetic acid, 3.7 kg/h of formic acid, 0.2 kg/h of water and 0.1 kg/h of high boilers was taken off at a temperature of 147° C. via line (28). From the phase separator (25), which was connected to the top of column (8) via line (24), an organic phase comprising 133.8 kg/h of MTBE, 0.5 kg/h of acetic acid, 0.2 kg/h of formic acid and 4.1 kg/h of water was recirculated via line (27) to the solvent inlet of the extractor (7). The stream of aqueous phase leaving the phase separator via line (26) was composed of 0.03 kg/h of acetic acid, 0.01 kg/h of formic acid, 4.1 kg/h of water and 0.1 kg/h of MTBE.

At the bottom of the distillation column (29), a stream comprising 12.6 kg/h of acetic acid and 0.1 kg/h of high boilers was taken off at a temperature of 154.1° C. via line (31). At the bottom of the pure acetic acid column (5), a stream comprising 0.06 kg/h of acetic acid and 0.1 kg/h of high boilers was taken off at a temperature of 143.6° C. via line (18).

The stream leaving the top of the pure formic acid column (33) via line (34) comprised 2.4 kg/h of formic acid. From the bottom of the pure formic acid column (33), a stream comprising 0.8 kg/h of acetic acid, 1.3 kg/h of formic acid and 0.2 kg/h of water was taken off at a temperature of 106.2° C. and recirculated via line (32) to the inlet of the solvent distillation column (8).

The aqueous stream leaving the bottom of the solvent stripping column (11) via line (13) comprised 48.4 kg/h of water, 0.4 kg/h of acetic acid, 0.2 kg/h of formic acid and 0.7 kg/h of high boilers. The return stream of organic phase via line (14) from the phase separation vessel (9) of the solvent stripper (11) to the solvent inlet of the extractor (7) was composed of 1.6 kg/h of MTBE, 0.01 kg/h of acetic acid, 0.01 kg/h of formic acid and 0.05 kg/h of water.

Fractionation of the crude acid mixture into 2.4 kg/h of 99.9% purity by weight formic acid, 12.5 kg/h of 99.9% purity by weight acetic acid and 49.6 kg/h of 97.5% purity by weight water required, without preheating of the feed upstream of the distillation columns, the following energy input:

bottom heating of the solvent distillation column (8): 20.5 kW bottom heating of the separation column (29): 10 kW bottom heating of the pure formic acid column (33): 5 kW bottom heating of the pure acetic acid column (5): 3.4 kW bottom heating of the solvent stripping column (11): 4 kW The total of 43 kW corresponds to 2.87 kW per kg of acid.

Example 2

In an apparatus corresponding to the embodiment shown in FIG. 3, a crude acid stream comprising 12.9 kg/h of acetic acid, 2.6 kg/h of formic acid, 48.4 kg/h of water and 0.8 kg/h of high boilers was fed via line (6) to the extractor (7) (countercurrent extraction column with stationary stainless steel packing, organic phase dispersed). A solvent return stream comprising 135.4 kg/h of methyl tert-butyl ether (MTBE), 4.0 kg/h of water, 0.5 kg/h of acetic acid and 0.2 kg/h of formic acid was fed to the extractor (7) via line (27) and line (14). The extract stream leaving the extractor (7) was composed of 133.9 kg/h of MTBE, 13.1 kg/h of acetic acid, 8.1 kg/h of water, 2.6 kg/h of formic acid and 0.1 kg/h of high boilers. The raffinate stream leaving the extractor (7) via line (15) was composed of 44.6 kg/h of water, 1.5 kg/h of MTBE, 0.4 kg/h of acetic acid, 0.2 kg/h of formic acid and 0.7 kg/h of high boilers.

The solvent distillation column (8) and the distillation column (29) were operated at a pressure of $1.0*10^5$ Pa. The pure formic acid column (33) was operated at a pressure of $0.25*10^5$ Pa. The pure acetic acid column (5) was operated at a pressure of $1*10^5$ Pa.

At the bottom of the solvent column (8), a stream comprising 13.4 kg/h of acetic acid, 3.7 kg/h of formic acid, 0.2 kg/h of water and 0.1 kg/h of high boilers was discharged at a temperature of 110° C. via line (28). From the phase separator (25), which was connected to the top of the column (8) via line (24), an organic phase comprising 133.8 kg/h of MTBE, 0.5 kg/h of acetic acid, 0.2 kg/h of formic acid and 4.0 kg/h of water was recirculated via line (27) to the solvent inlet of the extractor (7). The stream of aqueous phase leaving the phase separator via line (26) was composed of 0.03 kg/h of acetic acid, 0.01 kg/h of formic acid, 4.0 kg/h of water and 0.1 kg/h of MTBE.

At the bottom of the distillation column (29), a stream comprising 12.6 kg/h of acetic acid and 0.1 kg/h of high boilers was taken off at a temperature of 117.8° C. via line (31). At the bottom of the pure acetic acid column (5), a stream comprising 0.1 kg/h of acetic acid and 0.1 kg/h of high boilers was taken off at a temperature of 143.6° C. via line (18).

The stream leaving the top of the pure formic acid column (33) via line (34) comprised 2.4 kg/h of formic acid. A stream comprising 0.8 kg/h of acetic acid, 1.3 kg/h of formic acid and 0.2 kg/h of water was taken off at the bottom of the pure formic acid column (33) at a temperature of 68.6° C. and recirculated via line (32) to the inlet of the solvent distillation column (8).

The aqueous stream leaving the bottom of the solvent stripper column (11) via line (13) comprised 48.4 kg/h of water, 0.4 kg/h of acetic acid, 0.2 kg/h of formic acid and 0.7 kg/h of high boilers. The return stream of organic phase via line (14) from the phase separation vessel (9) of the solvent stripper (11) to the solvent inlet of the extractor (7) was composed of 1.6 kg/h of MTBE, 0.01 kg/h of acetic acid, 0.01 kg/h of formic acid and 0.01 kg/h of water.

Fractionation of the crude acid mixture into 2.4 kg/h of 99.9% purity by weight formic acid, 12.5 kg/h of 99.9% purity by weight acetic acid and 49.6 kg/h of 97.5% purity by weight water required, without preheating of the feed upstream of the distillation columns, the following energy input:

bottom heating of the solvent distillation column (8): 30 kW bottom heating of the separation column (29): 18 kW bottom heating of the pure formic acid column (33): 3 kW bottom heating of the pure acetic acid column (5): 5 kW bottom heating of the solvent stripping column (11): 4.5 kW The total of 60.5 kW corresponds to 4.05 kW per kg of acid.

Example 3

Figure 2:
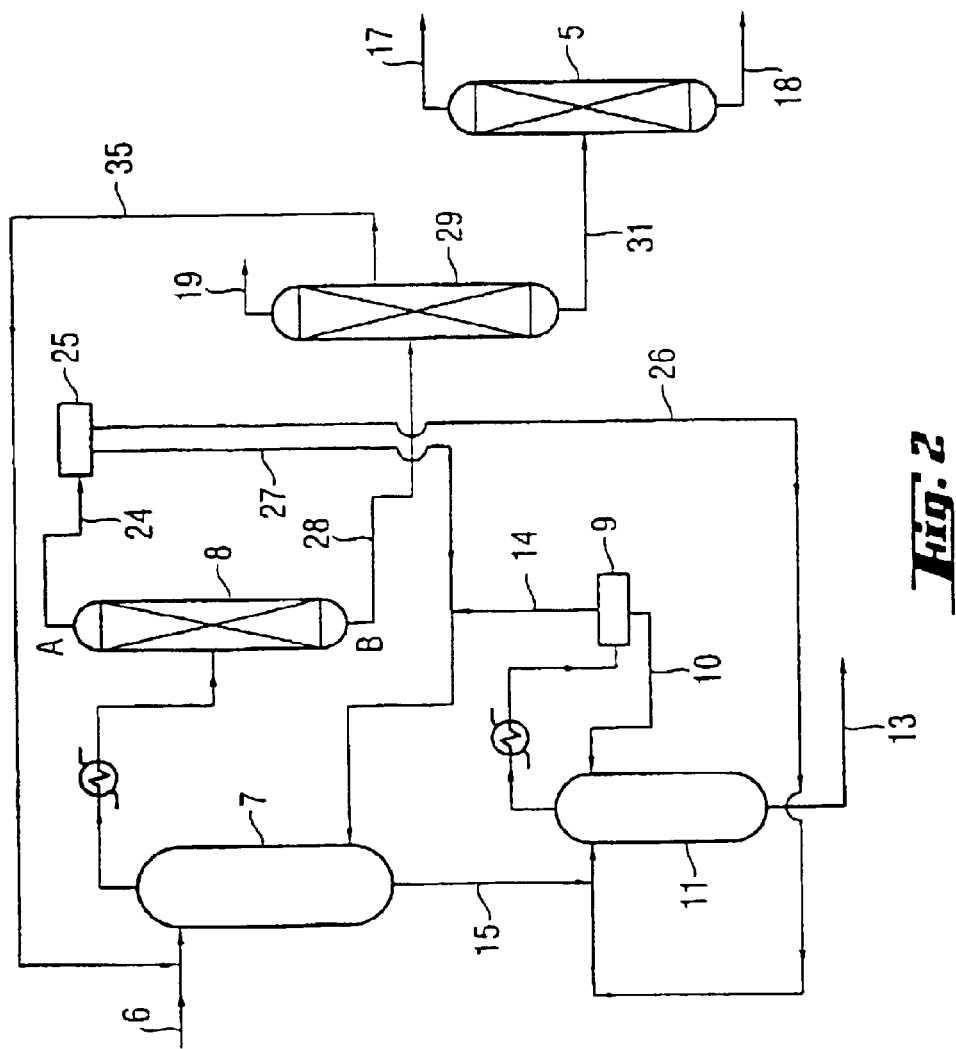
FIG. 2 shows the apparatus of FIG. 1 plus a recirculation back to the extractor.

In an apparatus corresponding to the variant shown in FIG. 2, a crude acid stream comprising 12.8 kg/h of acetic acid, 2.5 kg/h of formic acid, 48.6 kg/h of water and 0.8 kg/h of high boilers was fed via line (6) to the extractor (7) (countercurrent extraction column with stationary stainless steel packing, organic phase dispersed). A solvent return stream comprising 179.7 kg/h of methyl tert-butyl ether (MTBE), 1.9 kg/h of water, 0.4 kg/h of acetic acid and 0.1 kg/h of formic acid was fed to the extractor (7) via line (27) and line (14). The extract stream leaving the extractor (7) was composed of 178.3 kg/h of MTBE, 13.1 kg/h of acetic acid, 9.8 kg/h of water, 2.6 kg/h of formic acid and 0.2 kg/h of high boilers. The raffinate stream leaving the extractor (7) via line (15) was composed of 40.7 kg/h of water, 1.3 kg/h of MTBE, 0.2 kg/h of acetic acid, 0.1 kg/h of formic acid and 0.6 kg/h of high boilers.

The solvent distillation column (8) and the distillation column (29) were operated at a pressure of $2.75*10^5$ Pa. The pure acetic acid column (5) was operated at a pressure of $1*10^5$ Pa.

At the bottom of the solvent column (8), a stream comprising 12.6 kg/h of acetic acid, 2.4 kg/h of formic acid, 0.1 kg/h of water and 0.2 kg/h of high boilers was discharged at a temperature of 148.7° C. via line (28). The substream separated off at the top via line (24) was fed to the phase separator (25) and separated there. The organic phase obtained, comprising 177.9 kg/h of MTBE, 0.4 kg/h of acetic acid, 0.1 kg/h of formic acid and 1.8 kg/h of water, was recirculated to the extractor (7) via line (27). The stream of aqueous phase leaving the separator via line (26) was composed of 0.03 kg/h of acetic acid, 0.02 kg/h of formic acid, 7.8 kg/h of water and 0.4 kg/h of MTBE.

At the bottom of the distillation column (29), a stream comprising 12.5 kg/h of acetic acid, 0.01 kg/h of formic acid and 0.1 kg/h of high boilers was taken off at a temperature of 154.2° C. via line (31). At the bottom of the pure acetic acid column (5), a stream comprising 0.04 kg/h of acetic acid and 0.1 kg/h of high boilers was taken off at a temperature of 150° C. via line (18).

The stream leaving the top of the distillation column (29) via line (19) comprised 0.01 kg/h of acetic acid, 2.4 kg/h of formic acid and 0.01 kg/h of water. A side offtake stream comprising 0.05 kg/h of acetic acid, 0.8 kg/h of formic acid and 0.1 kg/h of water was taken from the column (29) via line (35).

The aqueous stream leaving the bottom of the solvent stripping column (11) via line (13) comprised 48.5 kg/h of water, 0.3 kg/h of acetic acid, 0.08 kg/h of formic acid and 0.6 kg/h of high boilers. The return stream of organic phase to the extractor via line (14) from the phase separation vessel (9) of the solvent stripper (11) was composed of 1.7 kg/h of MTBE, 0.01 kg/h of acetic acid, 0.01 kg/h of formic acid and 0.05 kg/h of water.

Fractionation of the crude acid mixture into 1.6 kg/h of 98.6% purity by weight formic acid, 12.5 kg/h of 99.99% purity by weight acetic acid and 49.4 kg/h of 98.1% purity by weight water required, without preheating of the feed upstream of the distillation columns, the following energy input:

bottom heating of the solvent distillation column (8): 22.5 kW bottom heating of the separation column (29): 10 kW bottom heating of the pure acetic acid column (5): 4 kW bottom heating of the solvent stripping column (11): 4.5 kW The total of 41 kW corresponds to 2.9 kW per kg of acid.

What is claimed is:

1. Process for the separation and purification of a mixture comprising main components acetic acid, formic acid, water and high boilers by extraction by means of a solvent in a circulation process in a first step and a subsequently fractionation of an extract stream in a sequence of distillation steps, which comprises feeding a raffinate stream containing a major part of water to a solvent stripping column (11) for removal of the water;

conveying an extract stream to a solvent distillation column (8) from which, in a first step, a mixture (A) comprising water and solvent is separated off via a top of column (8) and a mixture (B) comprising acetic acid, formic acid and high boilers is separated off via a bottom of column (8);

separating the formic acid off from the mixture (B) in intermediate distillation column (29) and subsequently fractionating a remaining mixture (B) into purified acetic acid and high boilers in an acetic acid distillation column (5), and conveying the mixture (A) to a phase separator (25) from which an aqueous phase containing residual solvent is recirculated to the solvent stripping column (11) and an organic phase is recirculated to an extractor (7).

2. Process according to claim 1, comprising operating the solvent distillation column (8) under atmospheric pressure.

3. Process according to claim 1, comprising operating the solvent distillation column (8) under a superatmospheric pressure of from $1*10^5$ to $50*10^5$ Pa.

4. Process according to claim 1, comprising operating the extractor (7) in at least one stage.

5. Process according to claim 1, wherein a solvent circuit in the extractor (7) runs countercurrent to crude acid.

6. Process according to claim 5, wherein the mixing ratio of solvent to crude acid (volume/volume) is from 0.5 to 20.

7. Process according to claim 1, wherein the solvent used is selected from the group consisting of a saturated hydrocarbon having from 4 to 8 carbon atoms, an unsaturated hydrocarbon having from 4 to 8 carbon atoms, a cyclic hydrocarbon having from 4 to 8 carbon atoms, and mixtures thereof.

8. Process according to claim 1, wherein the solvent used is at least one compound selected from the group consisting of ethers, esters, ketones, hydrocarbons and alcohols.

9. Process according to claim 1, wherein the solvent used is at least one compound selected from the group consisting of methyl tert-butyl ether, diisopropyl ether, di-n-propyl ether, ethyl butyl ether, ethyl acetate and isopropyl acetate.

10. Process according to claim 1, comprising carrying out the extraction at a temperature of from 0 to 60° C. and at a pressure of from $1*10^5$ to $20*10^5$ Pa.

11. Process according to claim 1, comprising operating the intermediate distillation column (29) at a pressure of from $1*10^5$ to $20*10^5$ Pa.

12. Process according to claim 1, comprising operating the solvent distillation column (8) so that water remains in a product stream.

13. Process according to claim 1, wherein the intermediate distillation column (29) has a side offtake at which a substream is taken off.

14. Process according to claim 1, wherein the mixture (B) comprising the components acetic acid, formic acid, high boilers and further residual water is fractionated in the intermediate distillation column (29) into a bottom product which is free of formic acid and comprises acetic acid and high boilers and a mixed top product comprising formic acid, water and acetic acid;

where a bottom product from the column (29) is fractionated in a downstream acetic acid distillation column (5) into purified acetic acid and high boilers and a top product from the intermediate distillation column (29) is fed to a purified formic acid distillation column (33) where it is fractionated into purified formic acid as top product and a mixed bottom product comprising acetic acid, formic acid and water which is recirculated to an extract stream to the solvent distillation column (8).

15. Process according to claim 14, comprising operating the purified formic acid distillation column (33) at a pressure which is from $0.1*10^5$ to $25*10^5$ Pa lower than a pressure in the intermediate distillation column (29).

16. Process according to claim 1, wherein heat of condensation in the distillation column (29) is used selected from the group consisting of heating a formic acid distillation column (33), heating the solvent stripping column (11), and heating both column (33) and column (11).

17. Process according to claim 1, wherein heat of reaction of an upstream reaction is used for heating at least one selected from the group consisting of the solvent distillation column (8), the distillation column (29), the acetic acid distillation column (5) and a formic acid distillation column (33).

* * * * *